United States Patent [19]

Loge et al.

[11] 4,398,885
[45] Aug. 16, 1983

[54] DENTAL HANDPIECE

[75] Inventors: Hans Loge, Biberach; Erich Bareth, Ummendorf, both of Fed. Rep. of Germany

[73] Assignee: Kaltenbach & Voigt GmbH & Co., Biberach an der Riss, Fed. Rep. of Germany

[21] Appl. No.: 296,053

[22] Filed: Aug. 25, 1981

[30] Foreign Application Priority Data

Feb. 6, 1981 [DE] Fed. Rep. of Germany ....... 3104239

[51] Int. Cl.$^3$ .............................................. A61C 1/08
[52] U.S. Cl. ...................................... 433/126; 433/29
[58] Field of Search ...................... 433/29, 32, 82, 99, 433/126, 132; 285/136; 350/96.22; 362/32

[56] References Cited

U.S. PATENT DOCUMENTS

| | | | |
|---|---|---|---|
| 3,582,637 | 6/1971 | Cecil, Jr. | 350/96.22 |
| 3,634,938 | 1/1972 | Hutchinson | 433/29 |
| 3,893,242 | 7/1975 | Lieb et al. | 433/29 |
| 3,897,134 | 7/1975 | Scrivo et al. | 433/29 |
| 3,951,514 | 4/1976 | Medina, Jr. | 350/96.22 |
| 4,027,938 | 6/1977 | Lewis | 350/96.22 |
| 4,080,737 | 3/1978 | Fleer | 433/126 |
| 4,124,271 | 11/1978 | Green | 350/96.22 |
| 4,140,366 | 2/1979 | Makuch et al. | 350/96.22 |
| 4,217,101 | 8/1980 | Loge | 433/126 |
| 4,260,382 | 4/1981 | Thomson | 433/29 |

Primary Examiner—John J. Wilson
Attorney, Agent, or Firm—Scully, Scott, Murphy & Presser

[57] ABSTRACT

There is disclosed a dental handpiece comprising a grip sleeve, a head portion provided at one end of the handpiece, a drive unit provided in the head portion for driving a dental implement, and a connecting portion arranged at an opposite end of the handpiece for rotation relative to the grip sleeve and releasably connected at one end to the grip sleeve. The connecting portion serves to convey operating media for the handpiece, and is adapted for connection at its other end to a supply tube for supplying the operating media. In order to provide built-in illumination in the region of the dental implement, an elongate photoconductive device is provided which extends generally longitudinally within the handpiece and includes, within the rotatable connecting portion, a light transmitting portion in the form of either a section of a strand like photoconductor, or an electrically operated bulb. The light transmitting portion is located, at least at the end of the connecting portion facing the grip sleeve, substantially centrally, whereby light can be transmitted along the photoconductive device, regardless of the rotational position adopted by the connecting portion relative to the grip sleeve.

12 Claims, 16 Drawing Figures

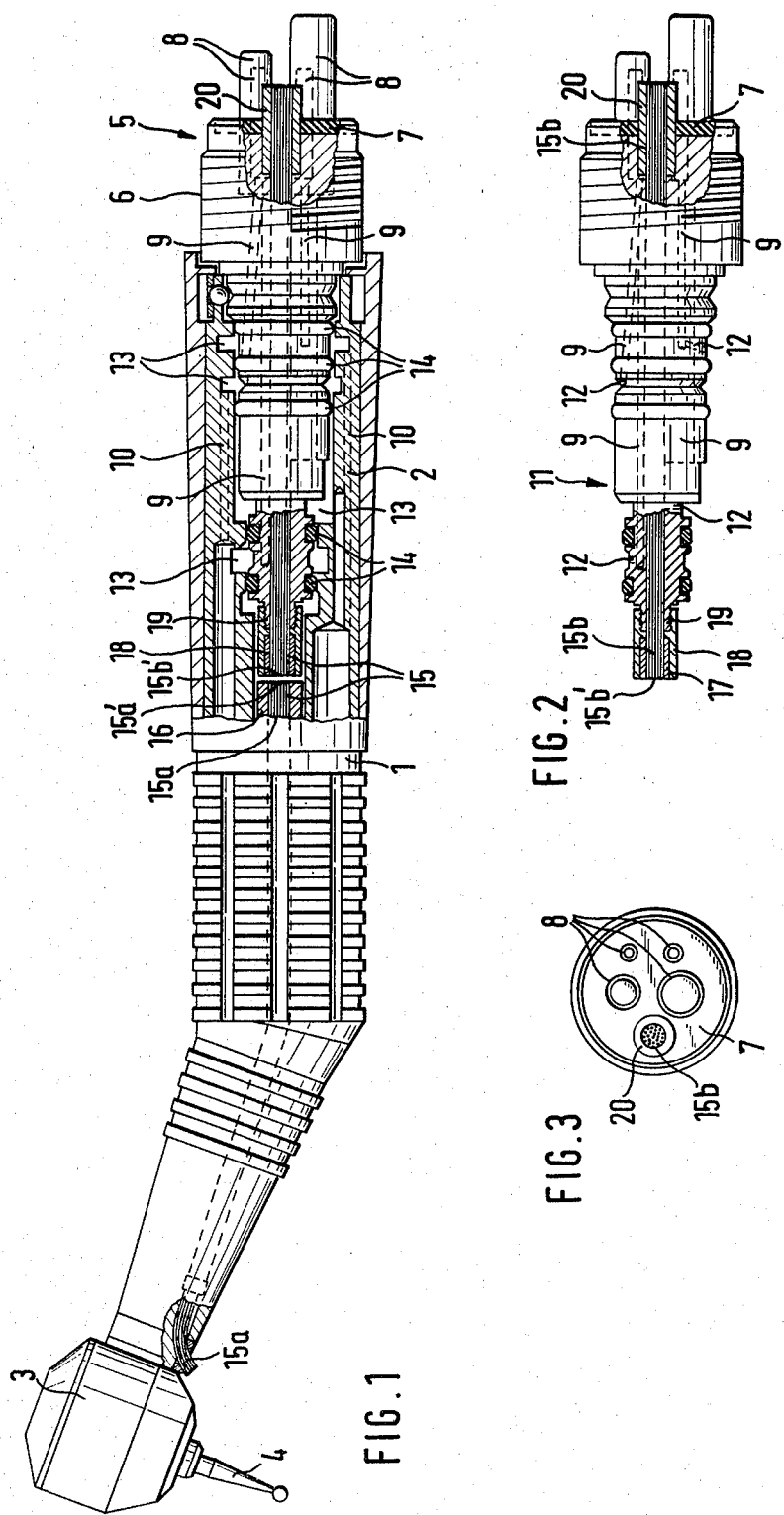

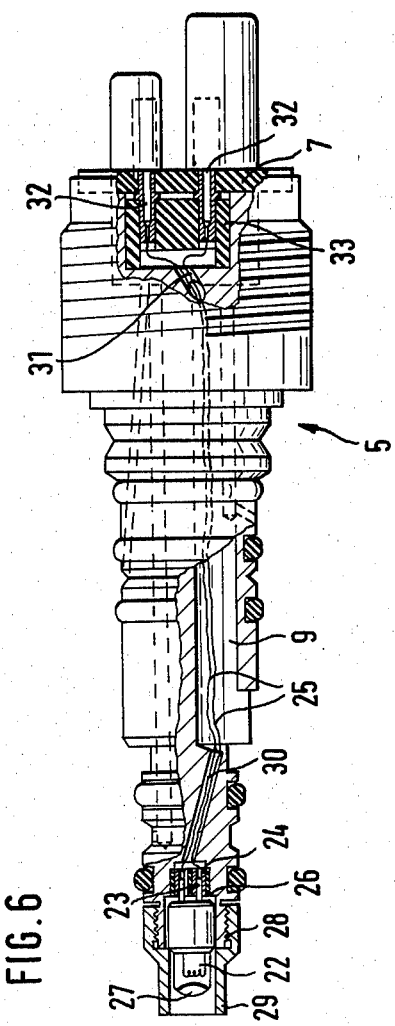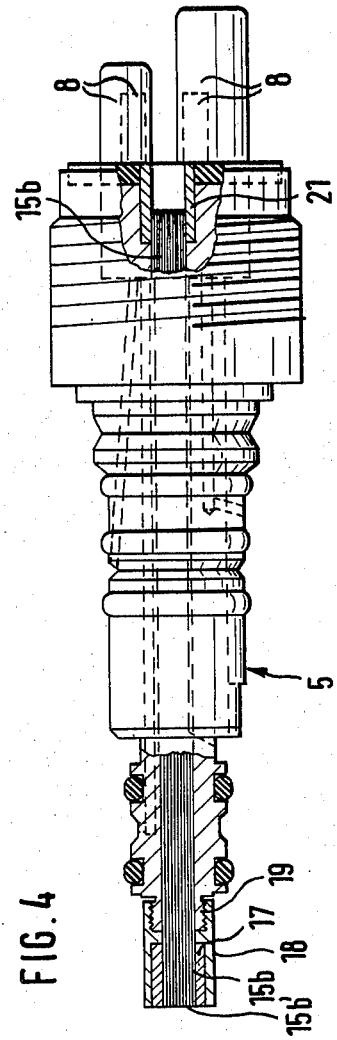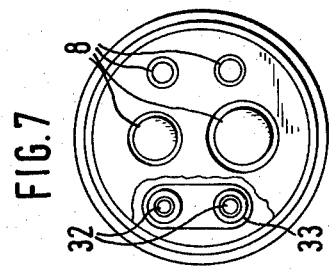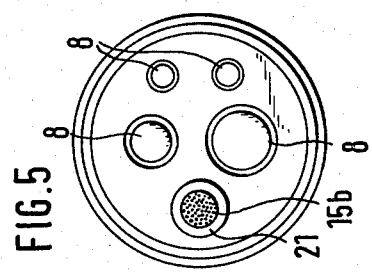

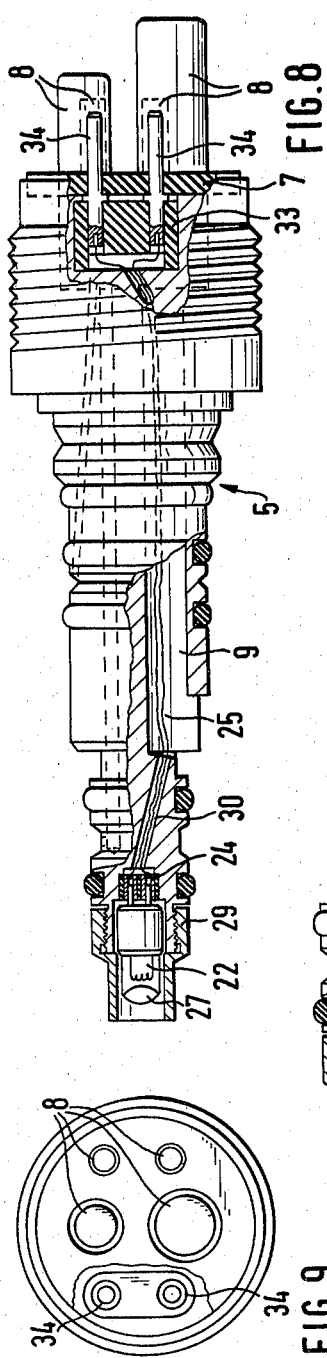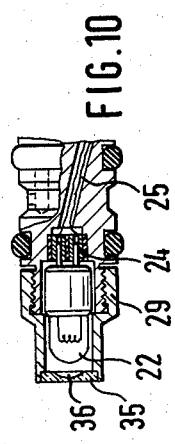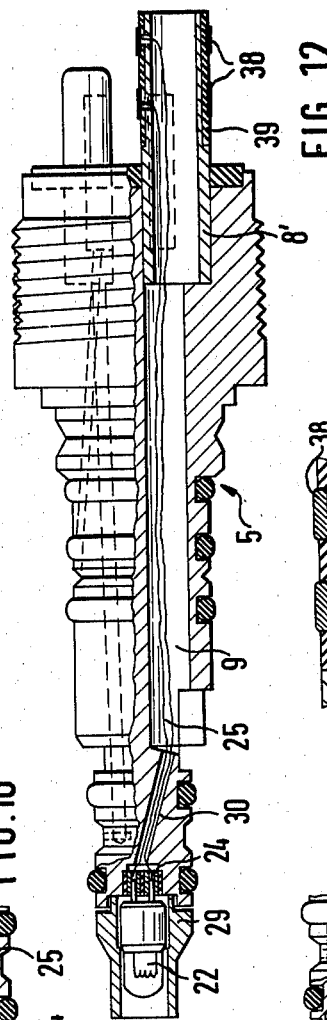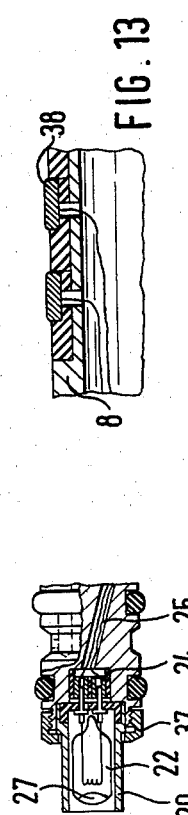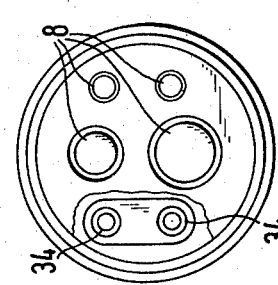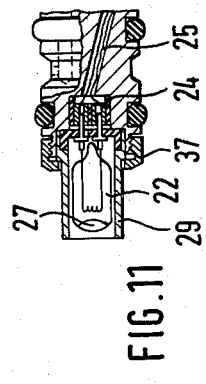

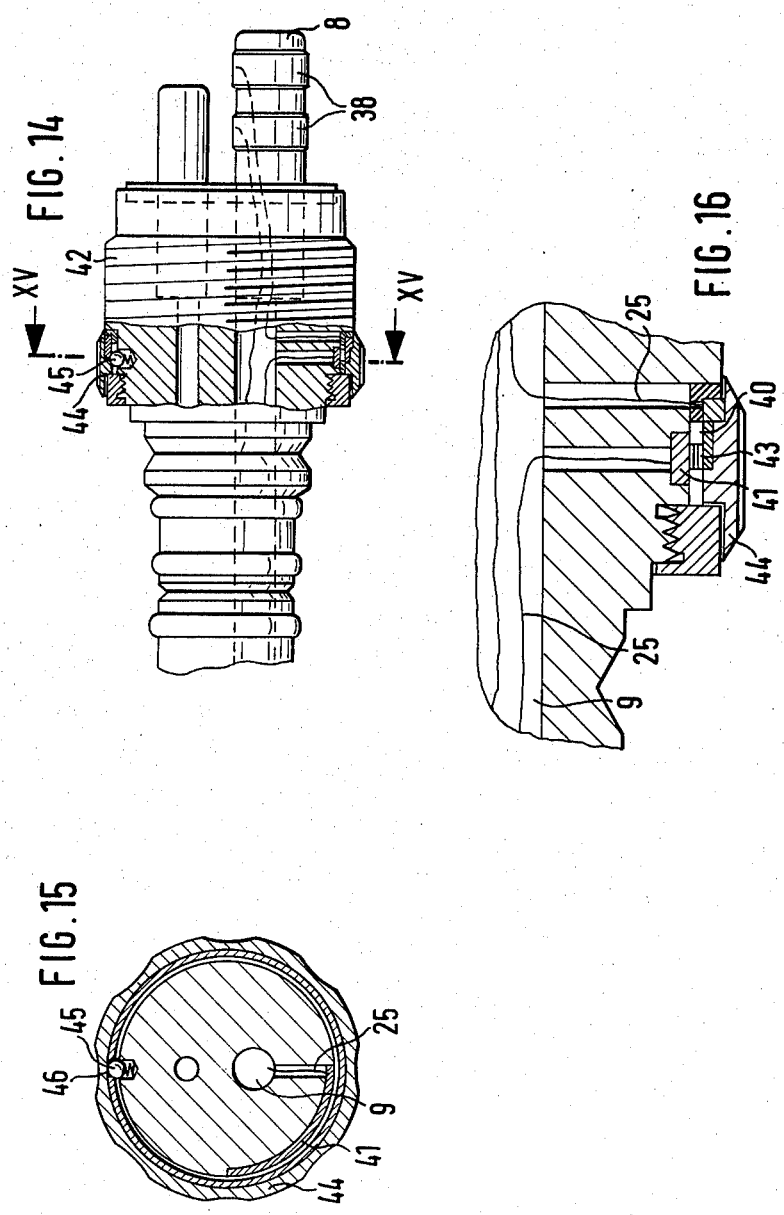

DENTAL HANDPIECE

This invention relates to a dental handpiece comprising a grip sleeve, a head portion provided at one end of the handpiece, a drive unit provided in the head portion for driving a dental implement when the latter is coupled with the drive unit, and a connecting portion arranged at an opposite end of the handpiece for rotation relative to the grip sleeve, the connecting portion being releasably connected at one end to the grip sleeve and being adapted for connection at its other end to a supply tube for supplying operating media for the handpiece in order to convey such media to points of usage in the handpiece.

A dental handpiece of the above type is known from DE-GM No. 77 29 110. However, the dentist giving treatment with this known handpiece has found again and again that although, due to the simple and free rotatability of the handpiece in relation to the connecting portion, and therefore in relation to the associated, relatively stiff supply tube, he was able to approach easily and without obstruction the point of the patient's tooth to be treated with the treating face of the tool, the fall of light on to the appropriate point, particularly when this was on the rear side of the tooth or on part of the tooth lying very deep or a long way back in the mouth, did, however, leave a great deal to be desired in the case of the light sources known up till now.

In order to remedy this, turbine dental handpieces have already been suggested, whereby one or several strand-like photoconductors, joined to the handpiece to make one unit, are provided, which are formed for example by a group of photoconductor fibres, whose end with the light outlet aperture is directed exactly on to the point to be treated, or respectively on to the dental tool.

A similar dental handpiece has thus become known from U.S. Pat. No. 3,397,457, whereby the strand-like photoconductor is arranged next to the ducts for water and compressed air inside the handpiece sleeve and the photoconductor leaves the supply tube shortly after its connection to the handpiece, whereupon the photoconductor is secured to the exterior of the supply tube along a certain length and is finally fed freely to a remote light source with appropriate control devices. The whole unit consisting of the dental handpiece and the combination of supply tube and photoconductor does however represent a somewhat rigid structure which is in itself unrotatable, and with which administering treatment to the patient is complicated and difficult.

Furthermore, a similar dental handpiece provided with two strand-like photoconductors is described in U.S. Pat. No. 3,614,414, whereby the photoconductors are secured to the exterior of the dental handpiece by means of brackets and also the complete light source is mounted on the rear end of the handpiece in the manner of a rucksack. Although, in this way, a change-over of the handpiece to photoconductors and a simplification of the whole arrangement in relation to expenditure on the light source can be effected without necessitating changes to the handpiece, yet the crucial disadvantage still remains even here, that due to the unrotatability of the handpiece-photoconductor-light source structure in itself, and due to two adjacently arranged, relatively rigid supply ducts, namely, on the one hand, the usual handpiece supply tube, and, on the other hand, the current cable leading to the light source, manipulating the dental handpiece when treating the patient is very difficult. Added to this is the fact that the photoconductors running outside the handpiece make it very difficult to grasp and hold the handpiece.

The same conditions also exist in the case of the dental handpiece according to U.S. Pat. No. 3,634,938, the only difference here being that the light source is designed as a rear portion of the handpiece, and therefore there is the possibility of using the cooling water duct for the additional purpose of cooling the incandescent bulb, i.e. the light source. The rigidity and unrotatability of this structure too with the disadvantages described above, still, however, remain, even with this known dental handpiece provided with a strand-like photoconductors.

Finally, a dental handpiece has become known from the publication HP-018G-0680-20M by the firm American Midwest, in which the strand-like photoconductor is accommodated in the handpiece together with the cooling water and compressed air supply tube end body. However, also in the case of this known handpiece, there is no free rotatability of the handpiece in relation to the associated supply tube, which is made more rigid by the photoconductor, with the result that in this case, too, easy manipulability of the handpiece is impaired.

The present invention has been developed primarily, though not exclusively, with a view to providing a handpiece of the above type, whereby, when it is used by the dentist, the point of the tooth to be treated is illuminated sufficiently in each case, and whereby, when a strand-like photoconductor, known in itself, is being used, the free rotatability of the handpiece in relation to the associated supply tube is in no way impaired, expenditure on construction for the handpiece itself is not increased by any great amount, and the easy exchangability of the parts of the handpiece in the area of the rotatable connection is maintained, so that the dental handpiece is operational even, for example, without the inclusion of a stand-like photoconductor.

According to the invention there is provided a dental handpiece comprising a grip sleeve; a head portion provided at one end of the handpiece; a drive unit provided in the head portion for driving a dental immplement when the latter is coupled with the drive unit; a connecting portion arranged at an opposite end of the handpiece for rotation relative to the grip sleeve, and releasably connected at one end to the grip sleeve and being adapted for connection at its other end to a supply tube for supplying operating media, such as compressed air and/or water, for the handpiece; first passages provided in the connecting portion for the conveyance of the media through the connecting portion; second passages provided in the grip sleeve and communicating with the first passages for all rotational positions of the connecting portion relative to the grip sleeve; and an elongate photoconductive device extending generally longitudinally of the handpiece and terminating near said head portion to provide illumination in the region of the dental implement;

in which the elongate photoconductive device extends at least partly within the handpiece and includes a light transmitting portion which extends within the connecting portion and is located, at least at the one end of the connecting portion, substantially on the axis of rotation of the connecting portion so that light can be transmitted along the photoconductive device for all rotational positions of the connecting portion relative to the grip sleeve.

In an embodiment of the invention, a strand-like photoconductor is arranged in the grip sleeve adjacent to the usual compressed air and cooling water ducts and, by virtue of the accommodation of the light transmitting portion inside the connecting portion, the supply tube (an end body thereof) can be coupled to the connecting portion so that the free rotatability of the handpiece remains unimpaired and so that much light still reaches the tool through the photoconductive device so that the point of the patient's tooth to be treated is completely illuminated. Added to this is the fact that, regardless of whether any strand-like photoconductor or an electrical light source together with connecting lines is contained in the connecting portion, it is possible, with each respective connecting portion, to exchange quickly and, for the dentist or his assistant, without difficulty, the parts of the light-transmitting portion and to rejoin the connecting portion to the grip sleeve, or respectively to the supply line.

BRIEF DESCRIPTION OF THE DRAWINGS

FIG. 1 is a side view, partly in section of an embodiment of dental handpiece having a light transmitting portion designed as a strand-like conductor and arranged in a detachable connecting piece of the handpiece;

FIG. 2 is a view of the connecting piece shown in FIG. 1;

FIG. 3 is an end view of the connecting piece;

FIG. 4 is a view to an enlarged scale, similar to FIG. 2, of a modified connecting piece;

FIG. 5 is an end view of the connecting piece shown in FIG. 4;

FIG. 6 is a side view, partly in section of a second construction of connecting piece of the dental handpiece, with a light transmitting portion designed as an incandescent bulb with connecting elements and arranged in the connecting piece;

FIG. 7 is an end view of the connecting piece shown in FIG. 6;

FIG. 8 is a view similar to FIG. 6, but showing a modified connecting portion to a supply tube for operating media of the handpiece, FIG. 9 is an end view of the connecting piece shown in FIG. 8;

FIG. 10 illustrates the left hand portion of the connecting piece shown in FIG. 8, with a modified design of the incandescent bulb shielding cap;

FIG. 11 illustrates a further modified design of the incandescent bulb shielding cap and the incandescent bulb according to FIG. 8;

FIG. 12 shows the connecting piece according to FIG. 6 or 8, but with a modified connecting portion to the supply tube;

FIG. 13 shows a detail of the connecting portion according to FIG. 12 in section;

FIG. 14 shows a further detail of the connecting portion of the connecting piece according to FIG. 12, designed as a light intensity adjusting device, partly in section, FIG. 15 is a section according to line XV—XV in FIG. 14, and FIG. 16 shows a detail of the light intensity adjusting device shown in FIG. 14 in section and on an enlarged scale.

DESCRIPTION OF PREFERRED EMBODIMENTS

The dental handpiece shown in FIG. 1 consists of a grip sleeve 1 with a grip sleeve body 2 arranged in this, which has a compressed-air-operated drive unit on its front end in a head part 3. This drive unit can be designed as an air motor or also as an air turbine, into whose long rotary shaft a dental tool 4 can be inserted. Set into the grip sleeve body 2 from its open side further away from the tool is a cylindrical connecting piece, which is releasable from the grip sleeve body 2 or respectively the grip sleeve 1, and which is freely rotatable in relation to the grip sleeve body 2, and to whose end further away from the tool an unshown flexible supply tube, conducting compressed air and other supply media to or from the grip sleeve 1, is connected releasably, but, in the shown case, unrotatably. For this purpose, the supply tube has, in a known manner, on its connection-sided end, a tube end body, which can be connected securely to the connecting piece 5, with the interposition of a sealing disc 7, by means of a coupling nut, which for its parts can be screwed on to an outer thread 6 of connecting piece 5.

The connecting piece 5 is provided with axially discharging and axially through-passing media through-flow channels 9 having four inlet pipes 8, which channels, when the grip sleeve 1 and the connecting piece 5 are connected, are connected to the media ducts 10 leading to the points of usage of the handpiece and arranged in the grip sleeve body 2. Of these media ducts, one can serve to supply drive air to the air turbine, the second to supply cooling water to the area of the dental tool 4, the third to supply cooling air to the area of the dental tool 4 and the fourth media duct 10 to remove waste air from the air turbine.

The connecting piece 5 is provided with a guide pin 11 introduced into an aperture of the grip sleeve body 2. The media through-flow channels 9 extend into the pin 11 with each end in outlet apertures 12 discharging from the circumference of the guide pin 11. These outlet apertures 12 are distributed over the length of the guide pin 11 with a mutual distance left between, and open into annular channels 13, which are sealed off from each other by means of sealing annuli 14 mounted in annular grooves of the guide pin 11. Originating in each case from these annular channels 13 are the media ducts 10 arranged axially in the grip sleeve body 2 and leding to the usage point of the handpiece.

In the embodiment shown in FIGS. 1 to 5 of the dental handpiece, the grip sleeve 1 and the connecting piece 5 releasably connected to it is penetrated over the whole length next to the media ducts 10 and the media through-flow channels 9 by a strand-like photoconductor 15, which leaves the grip sleeve 1 at the point of connection of the grip sleeve 1 to the head portion 3 in such a way that the beam of light leaving the photoconductor 15 is directed on to the operating surfaces of the dental tool 4, or respectively on to the point of the tooth to be treated. In the area of the face nearer the tool of the guide pin 11 of the connecting piece 5, which pin is inserted according to FIG. 1 into the corresponding axial aperture of the grip sleeve body 2 and held there by clamping with the aid of the flexible sealing annuli 14, the photoconductor 15 is introduced in the connecting piece 5, in such a manner as to be exactly central to its axis of rotation, and in the grip body, and is interrupted in the area in such a way that two photoconductor sections 15a and 15b are produced, whose faces 15a' and 15b', turned towards each other, lie close behind each other. The end of the photoconductor section 15a facing the connecting piece 5 is thereby held in a sleeve 16 and the adjacent end of the photoconductor section 15b held in a threaded sleeve 18 provided with a lining 17, which sleeve can be screwed on to a threaded pipe 19 arranged on the frontal face of the guide pin 11. This measure is provided in order that the photoconductor section 15b can be easily pulled out after the threaded collar 18 has been unscrewed, in the event of a repair.

The photoconductor 15 can be formed by a bunch of photoconductor fibres, e.g. made of glass, plastics or similar.

In order to be able to join the photoconductor section 15b at its rear end to the unshown end body of the supply tube, this photoconductor section 15b ends by closing off flush in a connecting pipe 20, which projects in front of the face of the connecting piece 5 further away from the tool, cf. FIGS. 1 and 2. In another embodiment of this connection, cf. FIG. 4, the rear end of the photoconductor section 15b can also end inwardly set back in a connecting socket 21, which closes flush with the face of the connecting piece 5 further away from the tool. As to which of the two types of connection to select, depends for example on the design of the supply tube end body.

Abutting as close as possible the, in FIG. 1, right end of the photoconductor section 15b is an unshown photoconductor, which is held first in the supply tube end body and is fed together with it through the supply tube or in a separate tube to an unshown light source.

In the second embodiment, shown in FIGS. 6 to 16, of the dental handpiece, there is housed, in place of the photoconductor section 15b in the connecting piece 5, a light source in the form of an electrical incandescent bulb 22, e.g. a halogen lamp, together with the plug-in elements 23, the connector socket 24 and the electrical lines 25 associated with it.

A connecting piece 5 is shown in FIGS. 6 and 7, whereby the plug socket 24 is introduced into the tool-sided end of the connecting piece 5 in an aperture 26, into which socket the incandescent bulb 22 can be inserted. This incandescent bulb 22 can, in order to concentrate the light emanating from it, be provided on its frontal face with a melted-on lens 27. Further concentration and straightening of the rays of light on to the rear face 15a' i.e. that further away from the tool, of the photoconductor section, is effected in that a cap 29, open to the front, and surrounding the incandescent bulb 22, can be screwed on to an outer thread 28 on the tool-sided end of the connecting piece 5. The cap 29, which can be set on to the connecting piece 5 can, however, also be provided with a translucent disc 35 with a melted-on lens 36—as can be seen from FIG. 10—in order to avoid fouling or oiling of the incandescent bulb 22 and the plug socket 24. Finally, as FIG. 11 shows, the cap 29 can also be secured to the connecting piece 5 by means of a coupling nut 37.

The electrical lines 25 connected to the plug socket 24 are first fed into an aperture 30, then into the waste air through-flow channel 9 and into an aperture 31 of the connecting piece 5 to inner plug sockets 32 arranged on the rear end of the connecting piece 5, which sockets are held in a support 33 arranged in a sunken manner in the rear face of the connecting piece 5, which penetrate the sealing disc 7 and which, according to FIG. 6, end flush with the latter. When connection of the electrical lines 25 to the unshown supply tube end body is required, the connecting elements, as FIG. 8 shows, can also be designed as electrical contact pins 34.

FIGS. 12 to 16 show the further possibility of connecting the electrical lines 25 for the incandescent bulb 22 to the connecting parts of the supply tube end body. The wiring is thereby modified in such a way that the two lines 25 in the waste air through-flow channel 9 are fed to the very end of the waste-air outlet pipe 8 and are each connected there to a contact annulus 38, which surrounds the waste air outlet pipe 8, with the interposition of a sealing sleeve 39, parallel to the other respective contact annulus 38 and arranged at a distance from this. Both contact annuli 38 are to be connected to corresponding connector parts in the unshown supply tube end body.

For the purpose of adjusting the light intensity of the electrical incandescent bulb 22, as can be seen from FIGS. 14 to 16, a potentiometer strip 14, connected to one of the conductive wires 25 is arranged in a groove 40 in the outer side of the rear cylindrical part 42 of the connecting piece 5, which strip co-operates with a control annulus 44, rotatably mounted on the cylindrical part 42 of the connecting piece 5 and containing the receiver contact 43. In order to releasably secure the control annulus 44 in a predetermined position, a ball detent 45 with a flexibly mounted ball is arranged in the cylindrical part 42 further underneath the control annulus 44, which ball engages into corresponding recesses 46 in the inside of the control annulus 44.

The connecting piece 5 can also be connected to the grip sleeve 1 in an unshown way by means of a bayonet lock, a threaded screw, a spring hook or similar. The connection of the connecting piece 5 to the supply tube can be designed, just as to the grip sleeve, to be easily removable and also rotatable, but also rigid.

We claim:

1. In a dental handpiece comprising a grip sleeve; a head part provided at a first end of said grip sleeve; a drive unit comprised of an air operated turbine provided in said head part for driving a dental tool; a connecting portion arranged at the second, opposite end of the grip sleeve for free rotation relative to the grip sleeve, and releasably connected to said second end to the grip sleeve, said connecting portion being connected at its opposite end to a supply tube for supplying operating media, such as compressed air and/or water, to the headpiece; first through-flow channels provided in said connecting portion for the conveyance of the media through the connecting portion, terminating respectively in outlet apertures and extending into annular channels, which are sealed one from each other and from which there proceed second media through-flow channels provided in the grip sleeve and communicating with said first channels for all rotational positions of the connecting portion relative to the grip sleeve; and an elongate photoconductive device extending generally longitudinally of the grip sleeve and leading out near said head part to provide illumination in the region of the dental tool such that the elongate photoconductive device extends at least partly within the grip sleeve and ends in the axis of rotation of the connecting portion at the tool-side end of the connecting piece; and a light dispensing element which extends within the connecting portion and is located, at its end at the grip sleeve, substantially on the axis of rotation of the connecting portion so that light can be transmitted along the photoconductive device for all rotational positions of the connecting portion relative to the grip sleeve, the improvement comprising:
   a. said first media through-flow channels in the area of their outlet apertures being radially directed and the sealing of the annular channels one from each other being by means of sealing annuli mounted in annular grooves of the connecting portion, situated on both sides of the outlet apertures;
   b. the releasing of the connecting portion from the grip sleeve being by socket-connection, the holding members of the socket-connection being by means of said sealing annuli;
   c. said sealing annuli also functioning as bearings which support and allow rotation of the connecting portion relative to the grip sleeve;
   d. the supply tube having a tube end which is releasably connected to the connecting portion; and
   e. the light dispensing element near the supply tube end of the connecting portion being provided with one or more connecting elements for releasable connection of the light dispensing element to the supply tube, said light dispensing element also including an electrically operated bulb, and a plug socket set into one end of said connecting portion to receive a plug element provided on said bulb, and a cap threaded to one end of the connecting portion to shield said bulb, and electrical lines for said bulb which extend from said plug socket at said one end of said connecting portion through said connecting portion, and said connecting elements being provided adjacent to an end of said connecting portion and connected to said electrical lines, and air supply and air exhaust ducts for said turbine being provided in the handpiece, and in which said air exhaust duct is used to accommodate said electrical lines, and wherein said connecting elements are designed as contact annuli, which are arranged parallel to each other and at a distance from each other on a turbine air outlet exhaust stack and are designed to be sealed in relation to the latter and can be brought into connection with corresponding connecting contacts provided on the end of said supply tube.

2. A dental handpiece according to claim 1, in which said light dispensing element comprises a section of a strand like photoconductor which extends throughout the length of said connecting portion and terminates at an end which is substantially flush with one end of the connecting portion.

3. A dental handpiece according to claim 2, in which one end of the connecting portion comprises a threaded sleeve which is screwed-on to a threaded pipe.

4. A dental handpiece according to claim 3, in which said threaded sleeve is provided with a lining.

5. A dental handpiece according to claim 2, in which one end of said photoconductor section is housed in a connecting pipe and closes-off flush with an end of a connecting pipe, said connecting pipe projecting from an end face of the connecting portion which is remote from said grip sleeve.

6. A dental handpiece according to claim 2, in which one end of said photoconductor section is set back inside a connecting socket, the connecting socket being arranged in said connecting portion so as to be flush with an end face of the connecting portion remote from the grip sleeve.

7. A dental handpiece according to claim 1, in which said bulb is provided on its frontal face with a melted-on lens.

8. A dental handpiece according to claim 1, in which an end of said cap facing said grip sleeve is provided with a translucent disc incorporating a lens.

9. A dental handpiece according to claim 1, in which said connecting elements are formed by plug sockets arranged in a sunken manner in the face of said connecting portion remote from the grip sleeve.

10. A dental handpiece according to claim 1, in which said connecting elements are formed by contact pins projecting out of the face of said connecting portion remote from the grip sleeve.

11. A dental handpiece according to claim 1, including a potentiometer strip inserted in one of the electrical lines for the purpose of light intensity adjustment, which strip is arranged in a groove in a cylindrical portion of said connecting portion and is surrounded by a control annulus with a receiver contact, and said annulus being secured in position by means of a ball-type detent.

12. A dental handpiece according to claim 1, in which said photoconductive device includes a group of optical fibres.

* * * * *